US012685551B2

(12) United States Patent
Farzin

(10) Patent No.: US 12,685,551 B2
(45) Date of Patent: Jul. 21, 2026

(54) ORAL CLEANING DEVICE FOR A BABY

(71) Applicant: Nina D. Farzin, Potomac, MD (US)

(72) Inventor: Nina D. Farzin, Potomac, MD (US)

( * ) Notice: Subject to any disclaimer, the term of this patent is extended or adjusted under 35 U.S.C. 154(b) by 122 days.

(21) Appl. No.: 18/380,749

(22) Filed: Oct. 17, 2023

(65) Prior Publication Data

US 2024/0122618 A1 Apr. 18, 2024

Related U.S. Application Data

(60) Provisional application No. 63/417,644, filed on Oct. 19, 2022, provisional application No. 63/416,924, filed on Oct. 17, 2022.

(51) Int. Cl.
*A61B 17/24* (2006.01)
*A46B 5/04* (2006.01)
(Continued)

(52) U.S. Cl.
CPC .............. *A61B 17/244* (2013.01); *A46B 5/04* (2013.01); *A46B 9/025* (2013.01); *A46B 9/026* (2013.01);
(Continued)

(58) Field of Classification Search
CPC ......... A61B 17/244; A61B 17/24; A46B 5/04; A46B 2200/1066; A46B 1/00;
(Continued)

(56) References Cited

U.S. PATENT DOCUMENTS 3,043,295 A 7/1962 Ward
4,628,949 A * 12/1986 Mas ........................ A45D 44/18
132/308
(Continued)

FOREIGN PATENT DOCUMENTS

CN 201422559 Y * 3/2010 ............... A46B 5/04
CN 306473146 S * 4/2021
(Continued)

OTHER PUBLICATIONS

FridaBaby Baby's First Toothbrush with Case, posted Oct. 31, 2018 [online], [retrieved May 22, 2025]. Retrieved from internet, https://www.amazon.ca/dp/BO7JXNL2F5 (Year: 2018).*
(Continued)

*Primary Examiner* — Katherine M Shi
(74) *Attorney, Agent, or Firm* — The Law Office of Patrick F. O'Reilly III, LLC

(57) ABSTRACT

An oral cleaning device for a baby is disclosed herein. The oral cleaning device includes a head portion, the head portion including one of: (i) at least one plurality of bristles for brushing gums and/or teeth of a baby, or (ii) at least one protrusion for scraping food particles and other matter from a tongue of the baby; and a body portion connected to the head portion, the body portion having a first end that is distal from the head portion and a second end that is proximal to the head portion, the first end being oppositely disposed relative to the second end, the body portion including a tapered finger recess for accommodating varying finger sizes of different users, the tapered finger recess having a cross-sectional area that gradually decreases in size from the first end to the second end.

18 Claims, 16 Drawing Sheets

(51) Int. Cl.
    *A46B 9/02*         (2006.01)
    *A46B 9/04*         (2006.01)
    *A46B 15/00*       (2006.01)

(52) U.S. Cl.
    CPC .......... *A46B 9/045* (2013.01); *A46B 15/0087*
        (2013.01); *A46B 2200/1066* (2013.01)

(58) Field of Classification Search
    CPC . A46B 15/0081; A46B 15/0087; A46B 5/023;
        A46B 15/0089; A46B 5/02
    See application file for complete search history.

(56) References Cited

U.S. PATENT DOCUMENTS

| | | | |
|---|---|---|---|
| 5,044,037 A * | 9/1991 | Brown | A46B 15/0042 |
| | | | 206/811 |
| 5,407,254 A * | 4/1995 | Hegemann | A46B 5/0012 |
| | | | 264/243 |
| D372,586 S | 8/1996 | Quintanilla | |
| 5,765,252 A | 6/1998 | Carr | |
| 5,826,599 A * | 10/1998 | Adams | A45C 11/008 |
| | | | 132/308 |
| D485,440 S | 1/2004 | Snaith | |
| D511,896 S | 11/2005 | Wu | |
| D525,433 S | 7/2006 | Barman | |
| D585,648 S | 2/2009 | Hegemann | |
| 7,895,695 B2 | 3/2011 | Bernini | |
| 9,320,348 B2 | 4/2016 | Sabet | |
| 9,480,605 B2 | 11/2016 | Farzin | |
| D827,306 S * | 9/2018 | Sabet | D4/103 |
| D848,748 S | 5/2019 | Sabet et al. | |
| 10,413,376 B2 | 9/2019 | Arzegar | |
| 10,561,230 B2 | 2/2020 | Sabet et al. | |
| 10,925,385 B2 | 2/2021 | Lehar | |
| D922,077 S | 6/2021 | Lehar | |
| D947,540 S | 4/2022 | Wang | |
| D968,624 S | 11/2022 | Farzin | |
| D999,919 S | 9/2023 | Farzin | |
| D1,012,506 S | 1/2024 | Zhuang | |
| D1,074,203 S | 5/2025 | Farzin | |
| 2002/0152538 A1* | 10/2002 | McDevitt | A46B 5/04 |
| | | | 2/163 |
| 2006/0010628 A1* | 1/2006 | Moskovich | A61B 17/244 |
| | | | 15/167.1 |
| 2009/0035048 A1* | 2/2009 | Safieh | A46B 5/04 |
| | | | 401/282 |
| 2013/0333134 A1* | 12/2013 | Herr | A46B 5/002 |
| | | | 15/167.2 |
| 2014/0223682 A1* | 8/2014 | Sabet | A46B 5/04 |
| | | | 15/167.1 |
| 2015/0127036 A1 | 5/2015 | Farzin | |
| 2016/0255948 A1* | 9/2016 | Capozza | A46B 5/04 |
| 2018/0103746 A1* | 4/2018 | Crowley | A46B 5/04 |
| 2020/0008565 A1* | 1/2020 | Lehar | A46B 5/04 |
| 2020/0221860 A1* | 7/2020 | Zwimpfer | A46B 5/026 |
| 2021/0059393 A1* | 3/2021 | Yang | A46B 7/04 |
| 2022/0125685 A1 | 4/2022 | Farzin | |

FOREIGN PATENT DOCUMENTS

| | | | |
|---|---|---|---|
| CN | 213909002 U * | 8/2021 | |
| CN | 214103603 U * | 9/2021 | |
| KR | 101858615 B1 * | 6/2018 | |

OTHER PUBLICATIONS

Baby Buddy Silicone Finger Toothbrush, Green, posted Apr. 6, 2014 [online], [retrieved Apr. 23, 2024]. Retrieved from internet, https:// www.amazon.ca/dp/BOOI80QC98/?th=1 (Year: 2014).

Restriction Requirement in U.S. Appl. No. 29/856,819, mailed on May 14, 2024.

Ex Parte Quayle Action in U.S. Appl. No. 29/856,819, mailed on Sep. 13, 2024.

Notice of Allowance in U.S. Appl. No. 29/856,819, mailed on Jan. 10, 2025.

* cited by examiner

ORAL CLEANING DEVICE FOR A BABY

CROSS-REFERENCE TO RELATED APPLICATIONS

This patent application claims priority to U.S. Provisional Patent Application No. 63/416,924, entitled "Finger Toothbrush For A Baby", filed on Oct. 17, 2022, and additionally claims priority to U.S. Provisional Patent Application No. 63/417,644, entitled "Tongue Cleaner For A Baby", filed on Oct. 19, 2022, all of the disclosures of which are herein expressly incorporated by reference in their entireties.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF DISCLOSURE

1. Field of the Disclosure

The disclosure generally relates to an oral cleaning device for a baby. More particularly, the disclosure relates to an oral cleaning device for a baby that is configured to accommodate varying finger sizes of different users.

2. Background

Oral hygiene is very essential to one's overall well-being. Conventional baby toothbrushes are known for brushing the gums and/or teeth of a baby. Some of these conventional baby toothbrushes are adapted to fit over a finger of a user (e.g., a parent or other caregiver). However, these conventional baby toothbrushes are not adapted to fit varying finger sizes of different users, which often results in a loose fitting toothbrush that is difficult for the user to manipulate in the mouth of the baby.

In addition, scraping one's tongue can prevent cavities as well as remove harmful bacteria that inflame gums. If proper oral hygiene is ignored, it can lead to other issues such as heart disease, cancer, and more. Young kids are not in a position to do dental care themselves.

Cleaning of a baby's tongue and gums is recommended each time after feeding. During the cleaning of a baby's tongue and gums, it is recommended that the baby is gently cradled in the parent's or other caregiver's arm. Then, damp gauze, a washcloth, or a baby tongue cleaner is used to gently massage the baby's gums, tongue, and inner cheeks.

Oral hygiene is very important for babies as the tongue is the main organ for sucking. The baby's tongue should be cleaned every day to reduce the risk of fungus, bacteria, or other germs. Newborn babies have a higher risk of oral thrush due to their immune system not being developed completely.

Conventional baby tongue scrapers are known for cleaning the tongue of a baby. However, these conventional baby tongue scrapers are not adapted to fit over varying finger sizes of different users, which makes it more difficult for the user to manipulate the tongue scraper effectively in the mouth of the baby.

Therefore, what is needed is an oral cleaning device for a baby that is configured to accommodate varying finger sizes of different users so that the user is able to more effectively brush the gums and/or teeth of a baby. Moreover, what is needed is an oral cleaning device for a baby that is configured to accommodate varying finger sizes of different users so that the user is able to more effectively clean the tongue of a baby. Furthermore, an oral cleaning for a baby is needed that is safe and comfortable for both the user and the baby.

SUMMARY OF THE DISCLOSURE

Accordingly, the present disclosure is directed to an oral cleaning device for a baby that substantially obviates one or more problems resulting from the limitations and deficiencies of the related art.

In accordance with one or more embodiments of the present disclosure, there is provided an oral cleaning device for a baby that includes a head portion, the head portion including one of: (i) at least one plurality of bristles for brushing gums and/or teeth of a baby, or (ii) at least one protrusion for scraping food particles and other matter from a tongue of the baby; and a body portion connected to the head portion, the body portion having a first end that is distal from the head portion and a second end that is proximal to the head portion, the first end being oppositely disposed relative to the second end, the body portion including a tapered finger recess for accommodating varying finger sizes of different users, the tapered finger recess having a cross-sectional area that gradually decreases in size from the first end to the second end.

In a further embodiment of the present disclosure, the oral cleaning device further comprises a stem portion connecting the head portion to the body portion, the stem portion extending from the second end of the body portion to the head portion so that the head portion of the oral cleaning device is spaced apart from a fingertip of a user to prevent an inadvertent biting of the fingertip of the user by the baby.

In yet a further embodiment, the head portion of the oral cleaning device comprises a concave inner surface and a convex outer surface, the convex outer surface being oppositely disposed relative to the concave inner surface.

In still a further embodiment, the head portion comprises the at least one plurality of bristles for brushing gums and/or teeth of the baby, and the at least one plurality of bristles are disposed on the concave inner surface of the head portion of the oral cleaning device.

In yet a further embodiment, the at least one plurality of bristles comprises a first plurality of bristles disposed in a central region of the concave inner surface of the head portion, a second plurality of bristles disposed in a first side region of the concave inner surface of the head portion, and a third plurality of bristles disposed in a second side region of the concave inner surface of the head portion.

In still a further embodiment, the second plurality of bristles are disposed at a first acute angle relative to the first plurality of bristles, and the third plurality of bristles are disposed at a second acute angle relative to the first plurality of bristles.

In yet a further embodiment, the first acute angle of the second plurality of bristles is generally the same as the second acute angle of the third plurality of bristles.

In still a further embodiment, the head portion of the oral cleaning device comprises a front surface and a rear surface, the front surface being oppositely disposed relative to the rear surface.

In yet a further embodiment, the head portion is in a shape of an animal head.

In still a further embodiment, the animal head forming the head portion is a bear head.

In yet a further embodiment, the rear surface of the head portion comprises a face of the bear head.

In still a further embodiment, the head portion comprises the at least one protrusion for scraping food particles and other matter from a tongue of the baby, and the at least one protrusion is disposed on the front surface of the head portion of the oral cleaning device.

In yet a further embodiment, the at least one protrusion comprises a first protrusion disposed in a central region of the front surface of the head portion, a second protrusion disposed above the first protrusion on the front surface of the head portion, and a third protrusion disposed above the second protrusion on the front surface of the head portion.

In still a further embodiment, the first protrusion, the second protrusion, and the third protrusion of the head portion are each semi-circular in shape, and the first protrusion, the second protrusion, and the third protrusion are arranged in a generally concentric arrangement.

In yet a further embodiment, the second protrusion has a second radius that is larger than a first radius of the first protrusion, and the third protrusion has a third radius that is larger than the second radius of the second protrusion.

In still a further embodiment, the tapered finger recess comprises a hemispherical end portion proximate to the second end of the body portion of the oral cleaning device.

In yet a further embodiment, the oral cleaning device is formed from a polymeric material.

In still a further embodiment, the polymeric material forming the oral cleaning device comprises silicone.

In yet a further embodiment, the polymeric material forming the oral cleaning device does not comprise latex, bisphenol A, or polyvinyl chloride.

It is to be understood that the foregoing general description and the following detailed description are merely exemplary and explanatory in nature. As such, the foregoing general description and the following detailed description should not be construed to limit the scope of the appended claims in any sense.

BRIEF DESCRIPTION OF THE SEVERAL VIEWS OF THE DRAWINGS

The device will now be described, by way of example, with reference to the accompanying drawings, in which.

Throughout the figures, the same parts are always denoted using the same reference characters so that, as a general rule, they will only be described once.

DETAILED DESCRIPTION OF ILLUSTRATED EMBODIMENT(S)

Figure 8:
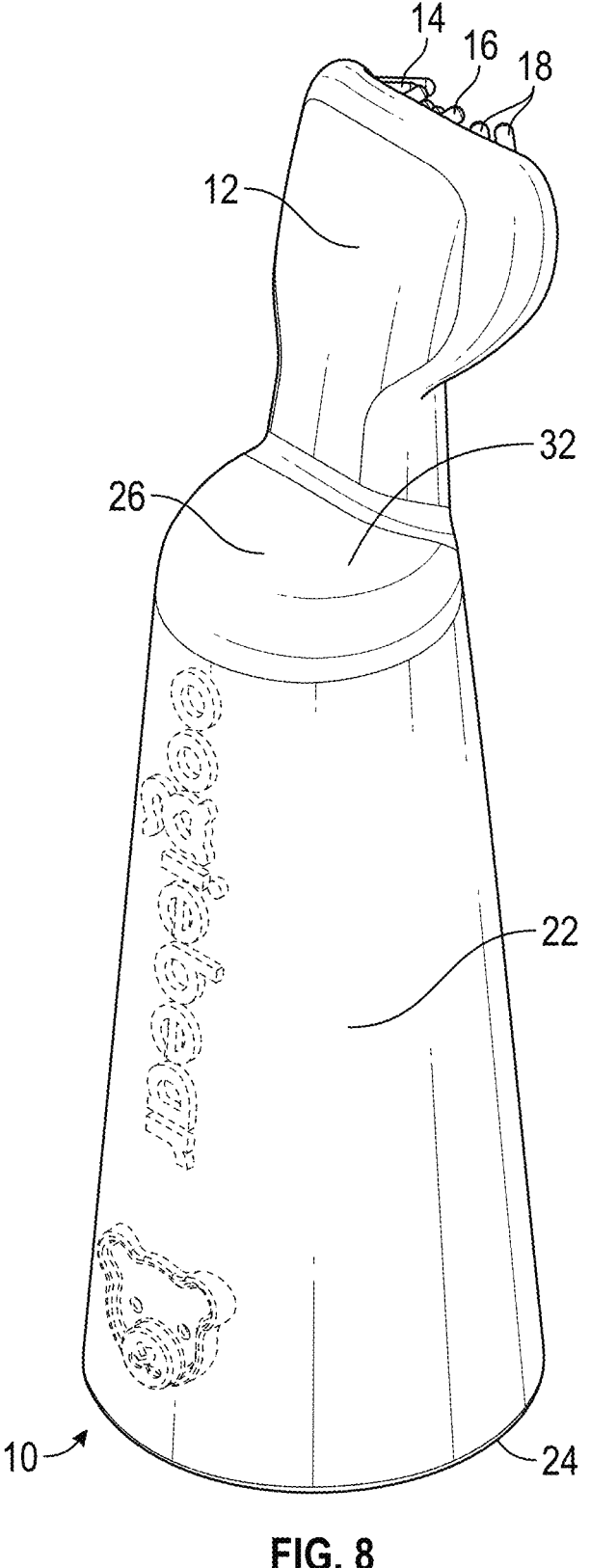
FIG. 8 is a rear perspective view of the oral cleaning device shown in FIG. 1.
Figure 9:
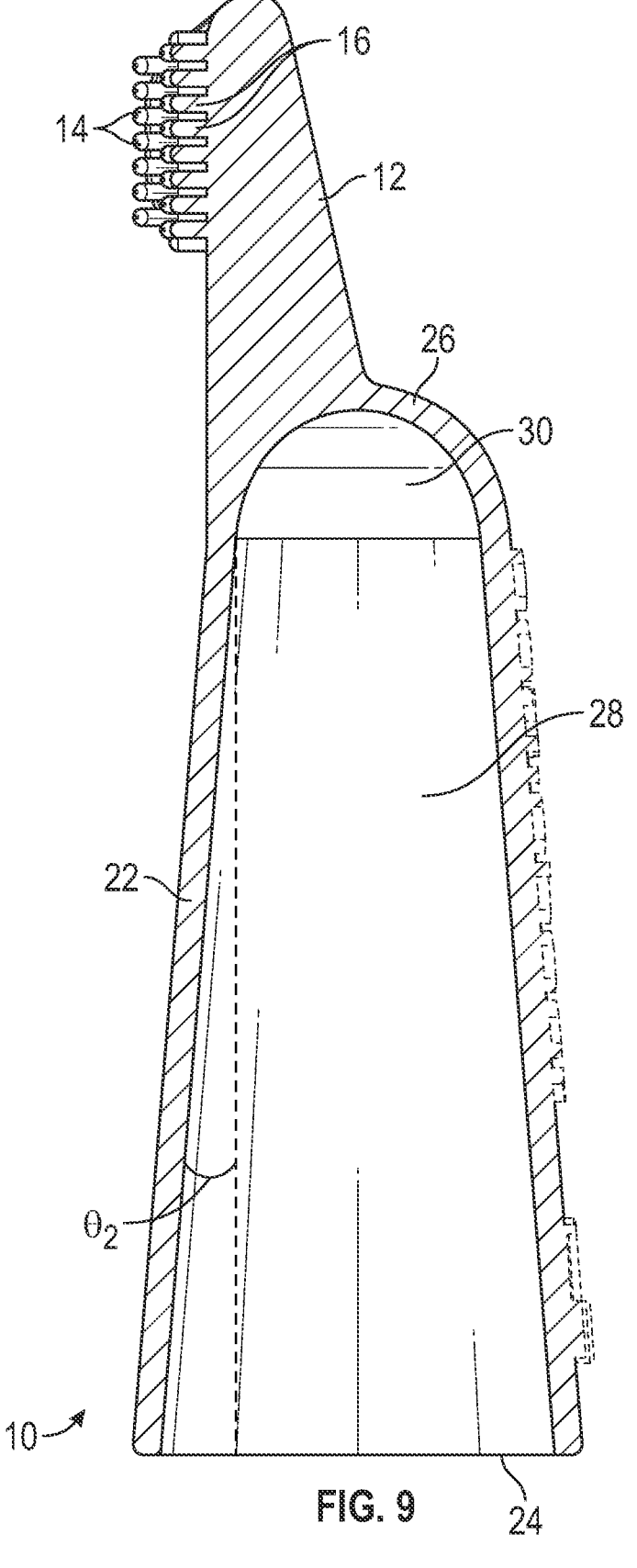
FIG. 9 is a longitudinal sectional view of the oral cleaning device shown in FIG. 1.

A first illustrative embodiment of an oral cleaning device for a baby is seen generally at 10 in FIGS. 1-9. With initial reference to FIGS. 1 and 2, it can be seen that the oral cleaning device 10 generally comprises a head portion 12, the head portion 12 including at least one plurality of bristles 14, 16, 18 for brushing gums and/or teeth of a baby; and a body portion 22 connected to the head portion 12, the body portion 22 having a first end 24 that is distal from the head portion 12 and a second end 26 that is proximal to the head portion 12, the first end 24 being oppositely disposed relative to the second end 26, the body portion 22 including a tapered finger recess 28 for accommodating varying finger sizes of different users, the tapered finger recess 28 having a cross-sectional area that gradually decreases in size from the first end 24 to the second end 26. For example, as shown in FIG. 9, the tapered finger recess 28 is bounded by an inwardly sloping wall that makes an acute angle $\theta_2$ with a vertical reference line. Also, in the illustrative embodiment, the tapered finger recess 28 may comprise a hemispherical end portion 30 proximate to the second end 26 of the body portion 22 of the oral cleaning device 10 (see FIG. 9). In the first illustrative embodiment, the oral cleaning device 10 may be in the form of a finger toothbrush 10 for brushing gums and/or teeth of a baby.

In the illustrative embodiment, referring again to FIGS. 1 and 2, it can be seen that the head portion 12 further comprises a stem portion 20 connecting the head portion 12 to the body portion 22. The stem portion 20 extends from the second end 26 of the body portion 22 to the head portion 12 so that the head portion 12 of the finger toothbrush 10 is spaced apart from a fingertip of a user to prevent an inadvertent biting of the fingertip of the user by the baby. As shown in FIG. 8, the body portion 22 further includes a ledge 32 at the second end 26 of the body portion 22, and the ledge 32 surrounds the stem portion 20 on a plurality of sides of the stem portion 20. Also, as shown in FIG. 1, the stem portion 20 comprises a curved base 34 that corresponds to a curvature of the hemispherical end cap at the second end 26 of the body portion 22, the curved base 34 having a wider diameter than a remainder of the stem portion 20.

Figure 1:
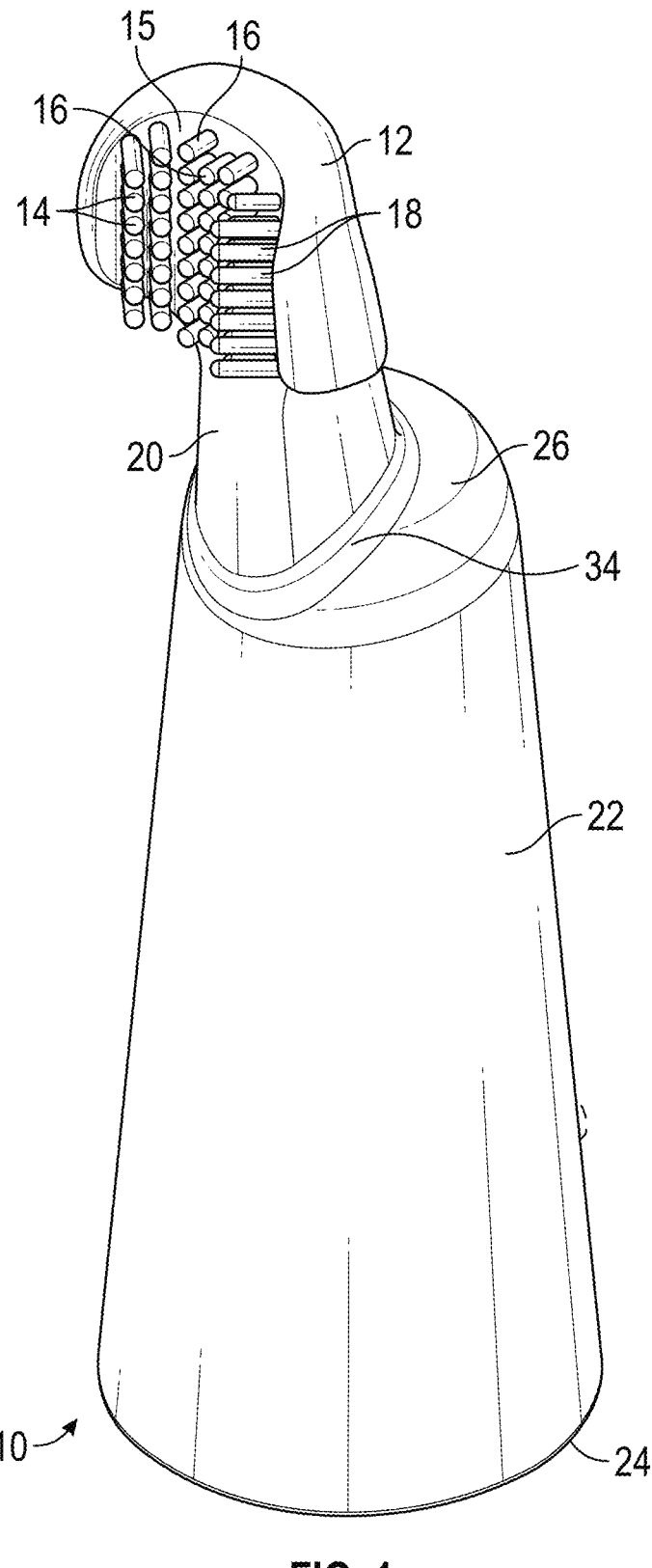
FIG. 1 is a frontal perspective view of an oral cleaning device for a baby, according to a first illustrative embodiment of the disclosure.
Figure 3:
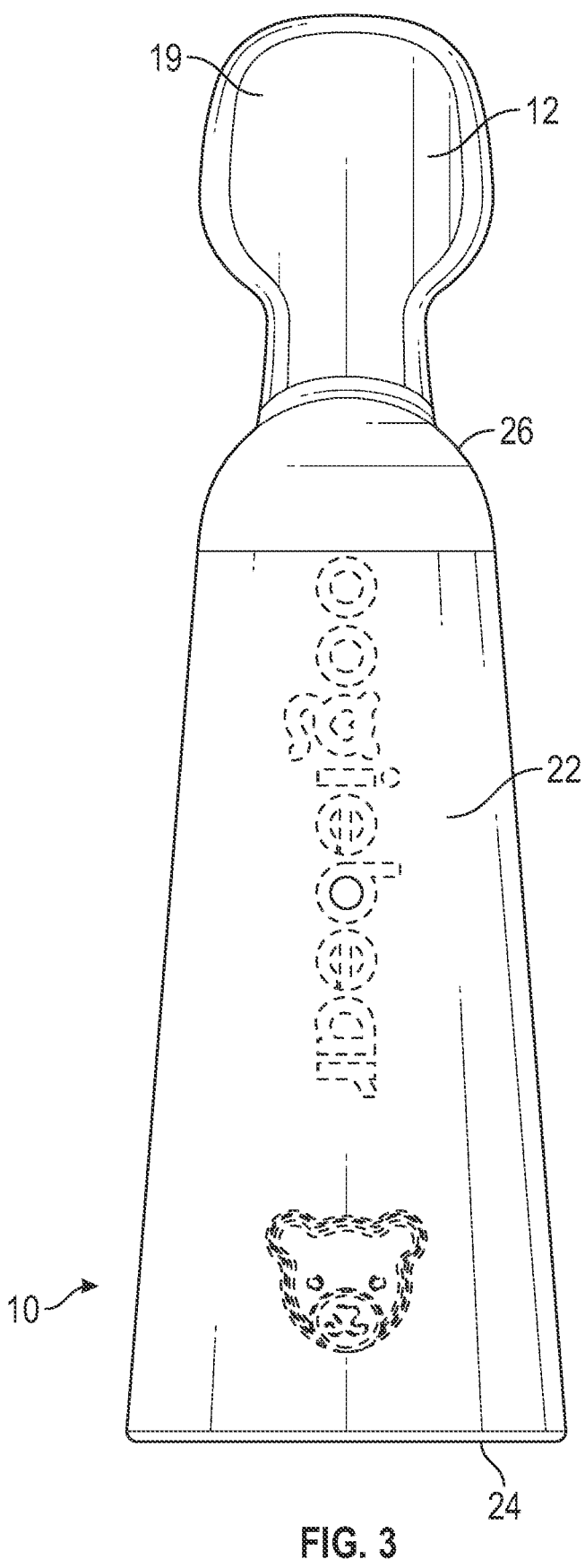
FIG. 3 is a rear elevational view of the oral cleaning device shown in FIG. 1.
Figure 4:
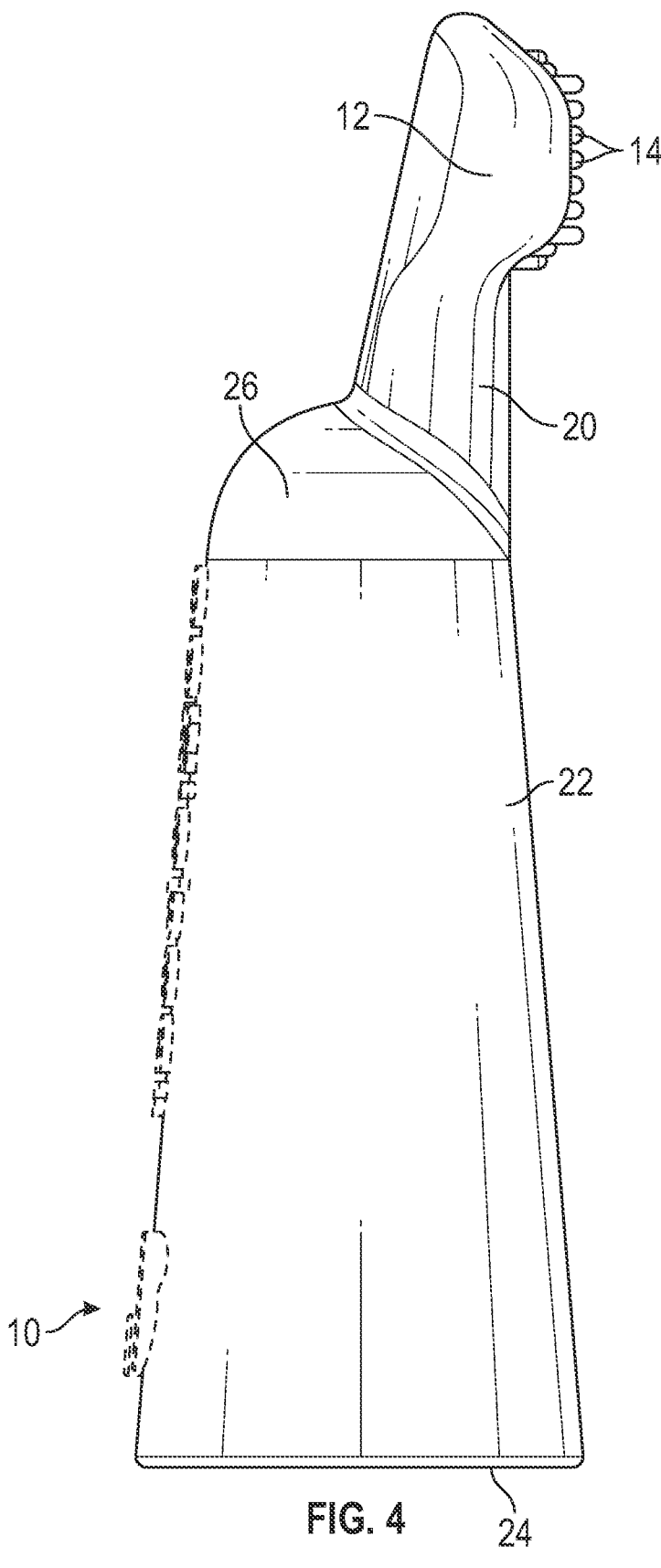
FIG. 4 is a first side view of the oral cleaning device shown in FIG. 1.
Figure 5:
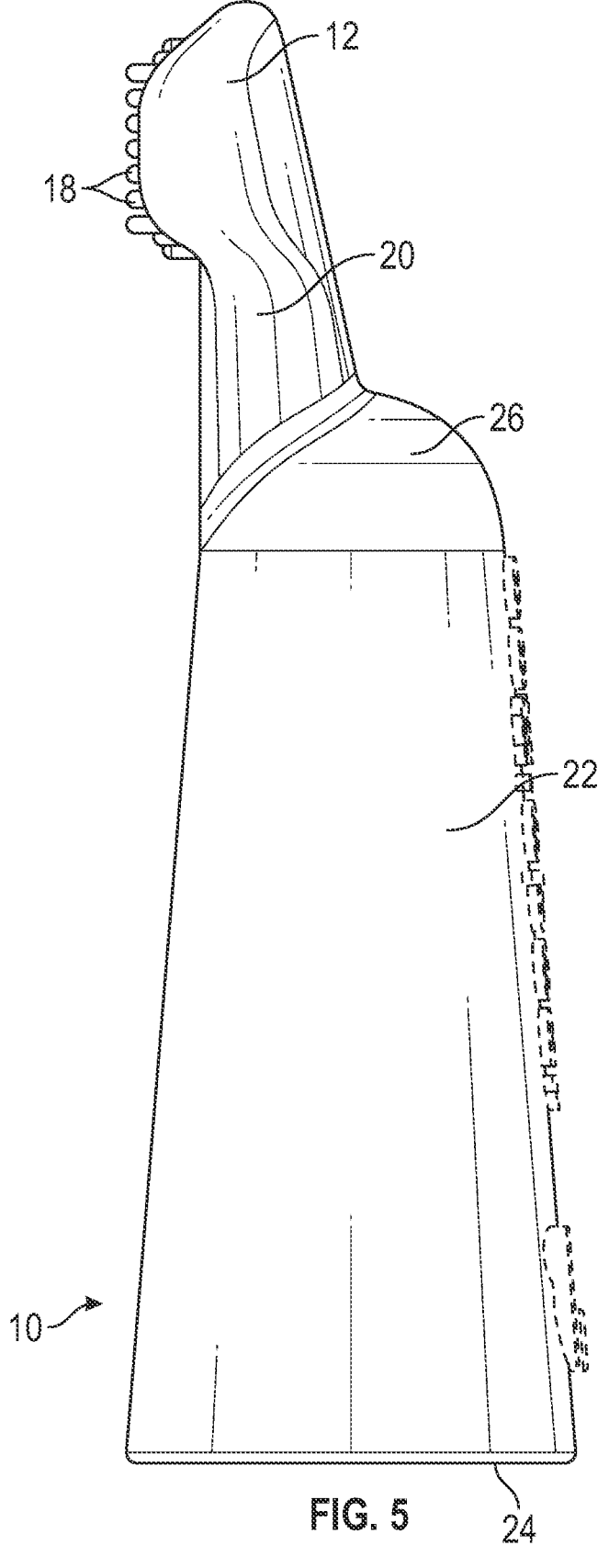
FIG. 5 is an opposite second side view of the oral cleaning device shown in FIG. 1.
Figure 6:
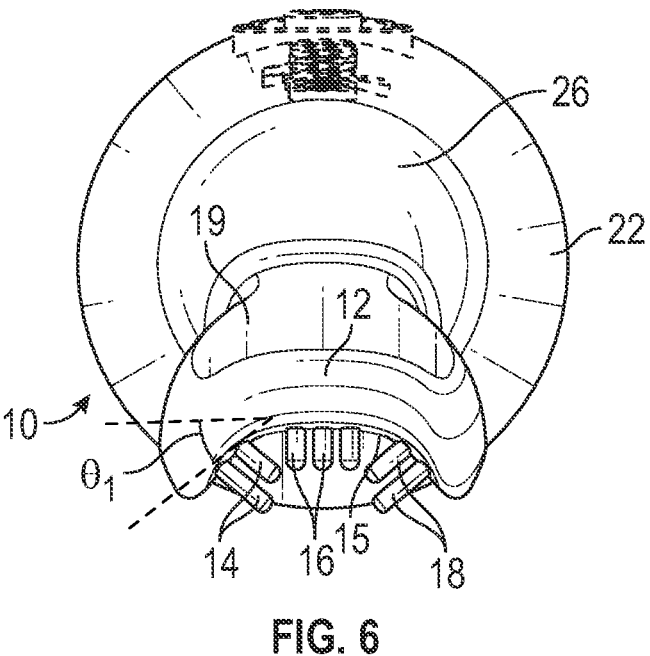
FIG. 6 is a top plan view of the oral cleaning device shown in FIG. 1.
Figure 7:
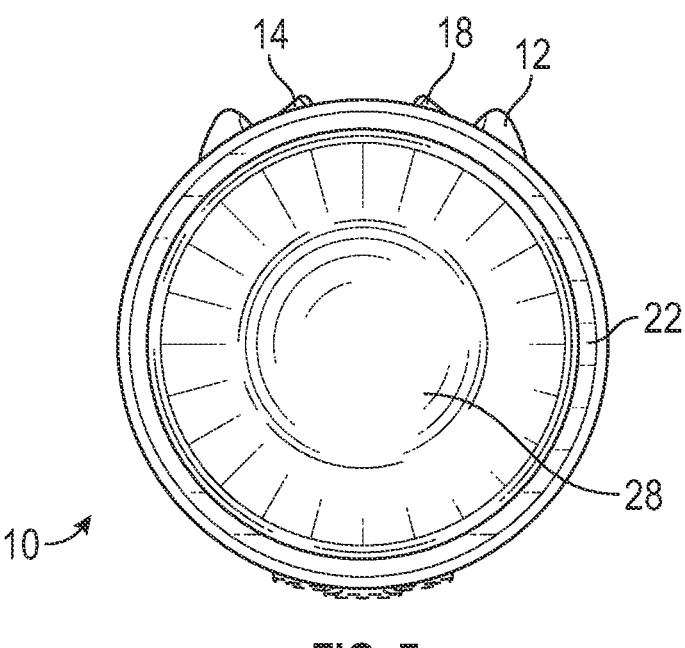
FIG. 7 is a bottom plan view of the oral cleaning device shown in FIG. 1.

With combined reference to FIGS. 1, 3, and 6, it can be seen that, in the illustrative embodiment, the head portion 12 of the oral cleaning device 10 comprises a concave inner surface 15 and a convex outer surface 19. The convex outer surface 19 is oppositely disposed relative to the concave inner surface 15. In the illustrative embodiment, as shown in FIG. 1, the at least one plurality of bristles 14, 16, 18 are disposed on the concave inner surface 15 of the head portion 12 of the oral cleaning device 10. Also, in the illustrative embodiment, the at least one plurality of bristles 14, 16, 18 comprises a first plurality of bristles 16 disposed in a central region of the concave inner surface 15 of the head portion 12, a second plurality of bristles 14 disposed in a first side region of the concave inner surface 15 of the head portion 12, and a third plurality of bristles 18 disposed in a second side region of the concave inner surface 15 of the head portion 12. In the illustrative embodiment, referring to FIGS. 1 and 6, the second plurality of bristles 14 are disposed at a first acute angle relative to the first plurality of bristles 16, and the third plurality of bristles 18 are disposed at a second acute angle relative to the first plurality of bristles 16. For example, as shown in FIG. 6, the first side region of the concave inner surface 15 from which the second plurality of bristles 14 extend is disposed at an acute angle $\theta_1$ (e.g., approximately 45 degrees) relative to the first plurality of bristles 16 disposed in the central region of the concave inner surface 15 of the head portion 12. In the illustrative embodiment, the first acute angle of the second plurality of bristles 14 is generally the same as the second acute angle of the third plurality of bristles 18. For example, as shown in FIG. 6, the second side region of the concave inner surface 15 from which the third plurality of bristles 18 extend is disposed at an acute angle relative to the first plurality of bristles 16 disposed in the central region of the concave inner surface 15 of the head portion 12, where the acute angle is also approximately equal to $\theta_1$ (e.g., approximately 45 degrees).

In the illustrative embodiment, the oral cleaning device 10 is formed from a polymeric material that does not comprise latex, bisphenol A (BPA), or polyvinyl chloride (PVC) (i.e., the material is latex-free, BPA-free, and PVC-free). More specifically, in the illustrative embodiment, the polymeric material forming the oral cleaning device 10 comprises silicone that does not contain latex, BPA, or PVC.

Figure 2:
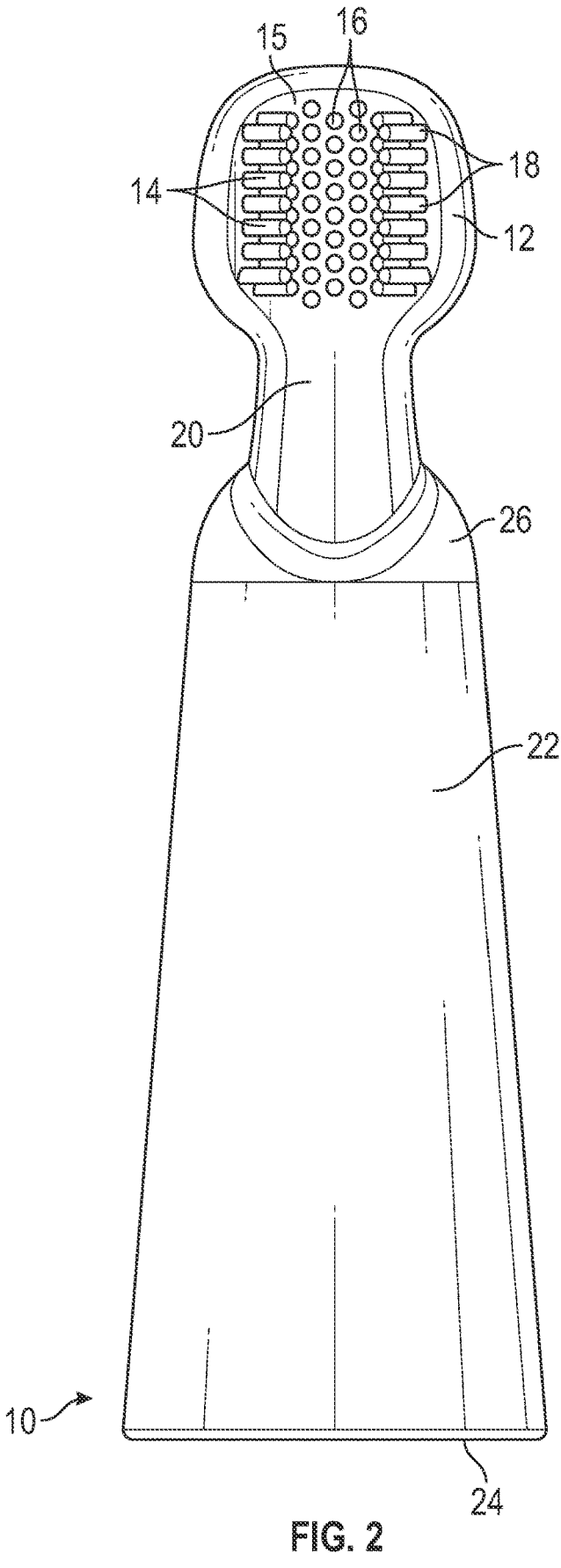
FIG. 2 is a front elevational view of the oral cleaning device shown in FIG. 1.

Now, with reference to FIGS. 1, 2, and 9, the manner in which the oral cleaning device 10 of the first illustrative embodiment is used will be described. First, a user (e.g., a parent or other caregiver) inserts one of his or her fingers into the tapered finger recess 28 of the body portion 22. Advantageously, the innovative tapered design of the finger recess 28 allows varying finger sizes of different users to be snugly received within the finger recess 28 (e.g., smaller fingers are inserted further into the tapered finger recess 28, while larger fingers are not inserted as far into the tapered finger recess 28). Then, the user (e.g., a parent or other caregiver) inserts the head portion 12 of the oral cleaning device 10 into a mouth of a baby to brush his or her gums and/or teeth. The brushing of the baby's gums and/or teeth is enhanced by the arrangement of the pluralities of bristles 14, 16, 18 on the concave inner surface 15 of the head portion 12 (i.e., because the bristles 14, 16, 18 are able to generally surround the teeth of the baby for better overall tooth surface coverage). The soft silicone material of the illustrative oral cleaning device 10 makes the oral cleaning device comfortable for the baby.

It is readily apparent that the aforedescribed oral cleaning device 10 offers numerous advantages. As described above, the oral cleaning device 10 is configured to accommodate varying finger sizes of different users so that the user is able to more effective brush the gums and/or teeth of a baby (i.e., the size of the finger recess 28 narrows to allow virtually any size finger to fit comfortably). Further, the oral cleaning device 10 is safe and comfortable for both the user and the baby. In the illustrative embodiment, the oral cleaning device 10 is formed from a flexible material that is gentle, safe, and firm enough to brush effectively. Also, in the illustrative embodiment, the oral cleaning device 10 is advantageously reusable, washable, and environmentally friendly.

In one or more illustrative embodiments, the aforedescribed oral cleaning device 10 helps to ensure healthy hygiene. Parents are able to begin a healthy dental hygiene regime from the beginning of their child's life so as to promote better oral health care early on. The oral cleaning device 10 is lightweight and easy to clean, which makes it handy for home or on the go. The oral cleaning device 10 is in a form of a durable, reusable tool that is made of high quality material(s) and cleans easily with soap and water. Because the head portion 12 of the oral cleaning device 10 is spaced apart from a fingertip of a user, the inadvertent biting of user's finger is prevented by the oral cleaning device 10, thereby advantageously resulting in a pain-free cleaning experience for the user (e.g., the parent or other caregiver).

Figure 18:
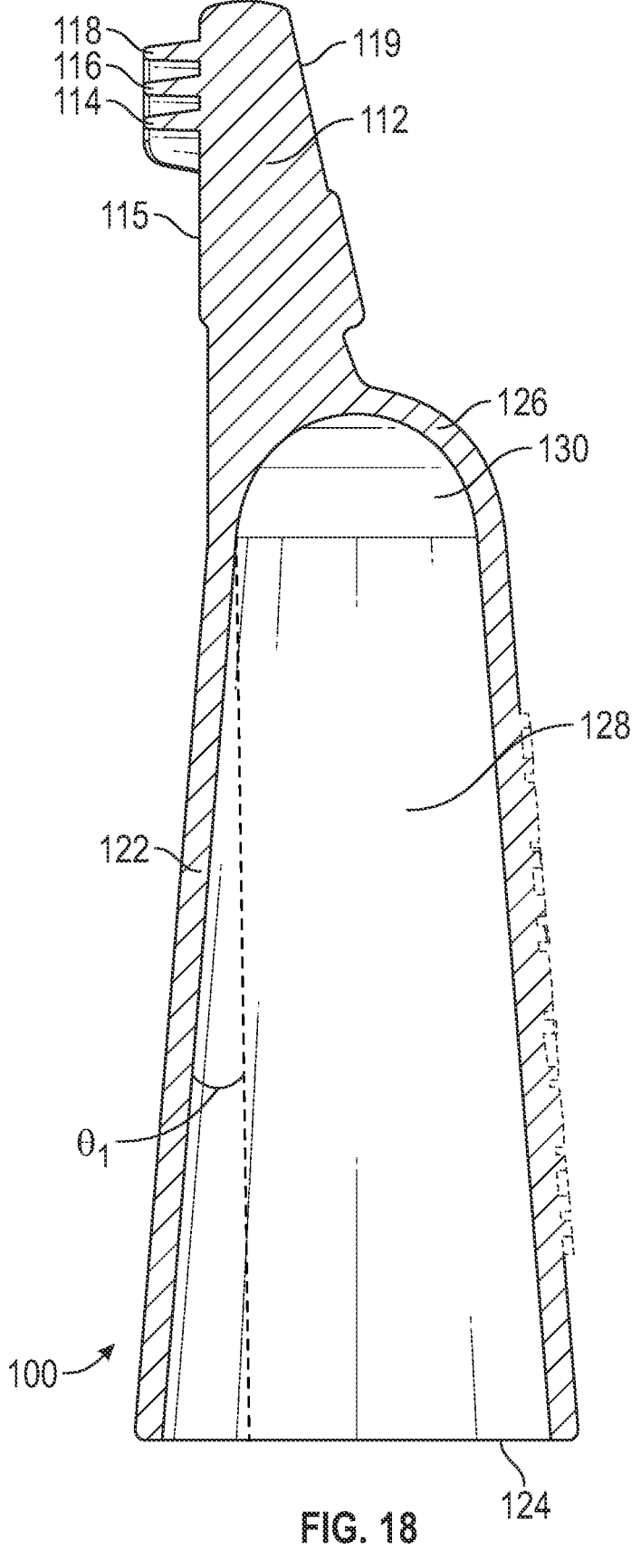
FIG. 18 is a longitudinal sectional view of the oral cleaning device shown in FIG. 10.

A second illustrative embodiment of an oral cleaning device for a baby is seen generally at 100 in FIGS. 10-18. With initial reference to FIGS. 10 and 11, it can be seen that the oral cleaning device 100 generally comprises a head portion 112, the head portion 112 including at least one protrusion 114, 116, 118 for scraping food particles and other matter from a tongue of a baby; and a body portion 122 connected to the head portion 112, the body portion 122 having a first end 124 that is distal from the head portion 112 and a second end 126 that is proximal to the head portion 112, the first end 124 being oppositely disposed relative to the second end 126, the body portion 122 including a tapered finger recess 128 for accommodating varying finger sizes of different users, the tapered finger recess 128 having a cross-sectional area that gradually decreases in size from the first end 124 to the second end 126. For example, as shown in FIG. 18, the tapered finger recess 128 is bounded by an inwardly sloping wall that makes an acute angle $\theta_1$ with a vertical reference line. Also, in the illustrative embodiment, the tapered finger recess 128 may comprise a hemispherical end portion 130 proximate to the second end 126 of the body portion 122 of the oral cleaning device 100 (see FIG. 18). In the second illustrative embodiment, the oral cleaning device 100 may be in the form of a tongue cleaner for scraping food particles and other matter from a tongue of a baby.

In the illustrative embodiment, referring again to FIGS. 10 and 11, it can be seen that the head portion 112 further comprises a stem portion 120 connecting the head portion 112 to the body portion 122. The stem portion 120 extends from the second end 126 of the body portion 122 to the head portion 112 so that the head portion 112 of the oral cleaning device 100 is spaced apart from a fingertip of a user to prevent an inadvertent biting of the fingertip of the user by the baby.

Figure 13:
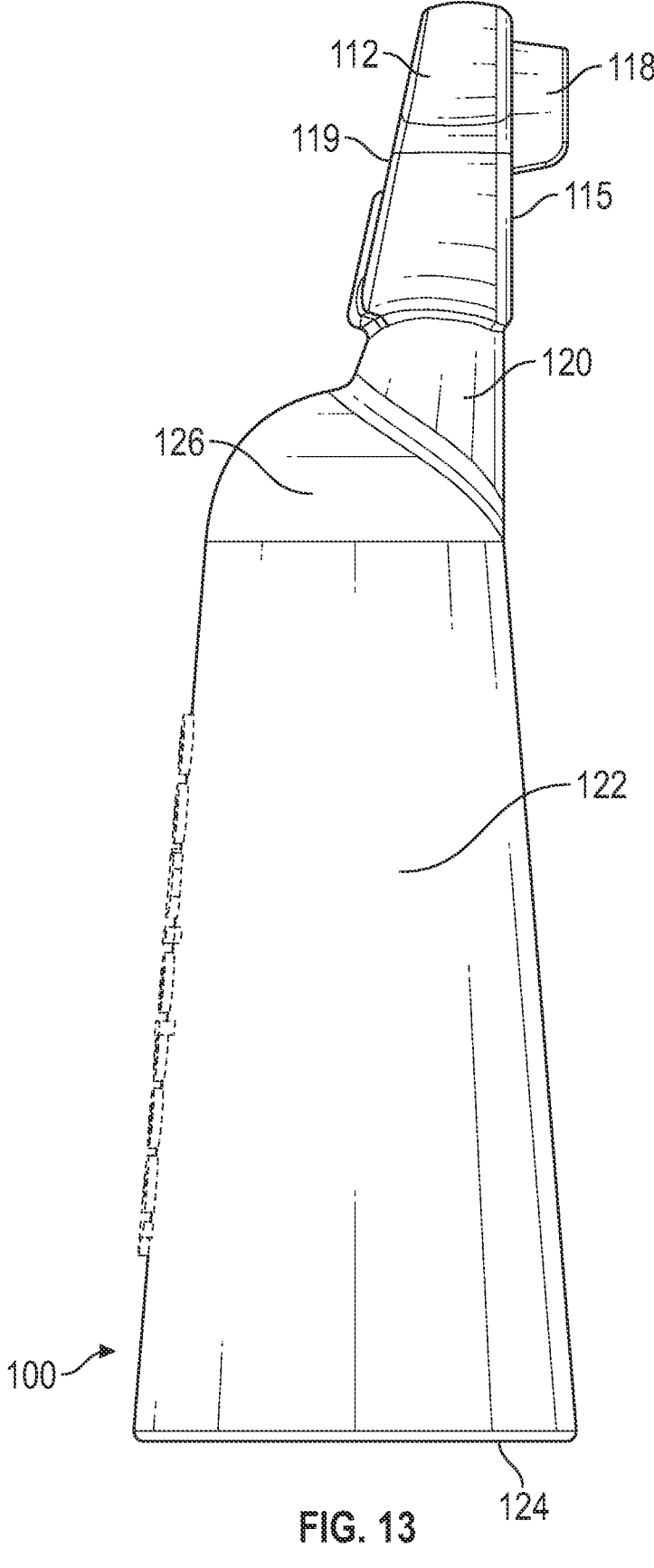
FIG. 13 is a first side view of the oral cleaning device shown in FIG. 10.
Figure 14:
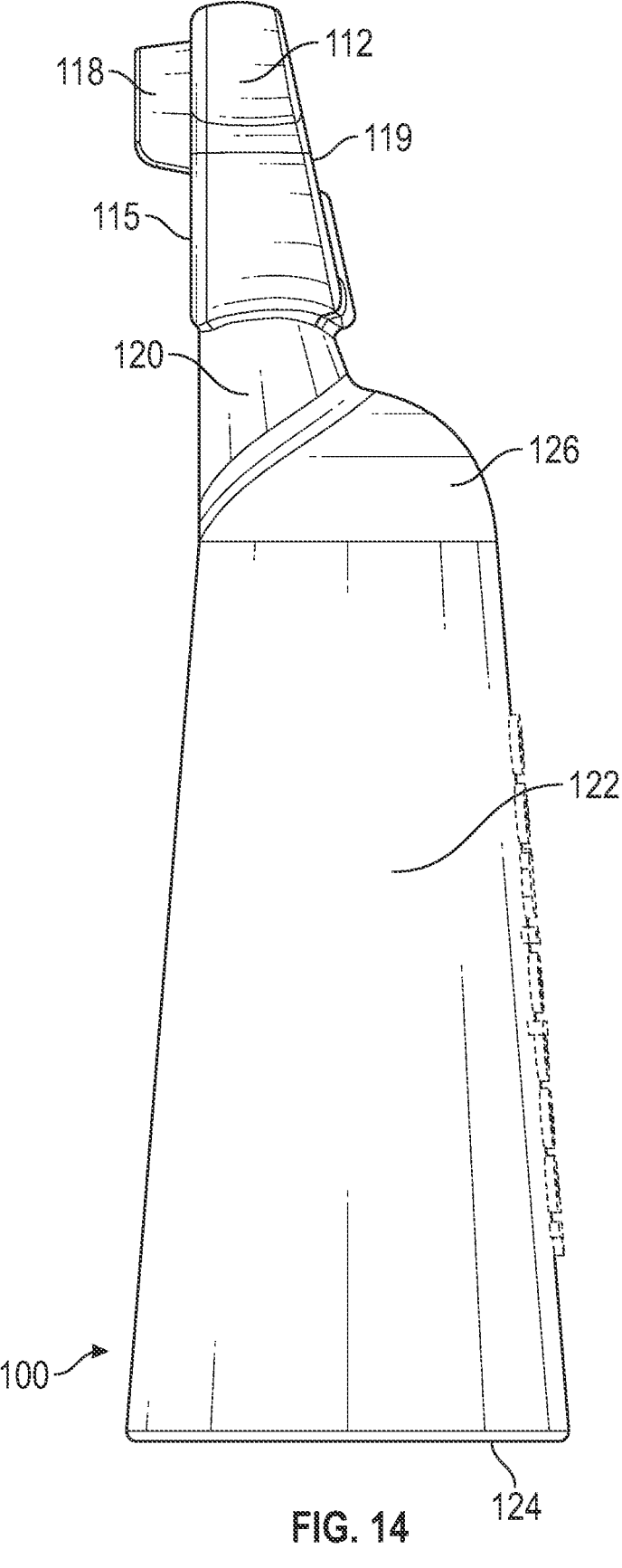
FIG. 14 is an opposite second side view of the oral cleaning device shown in FIG. 10.
Figure 15:
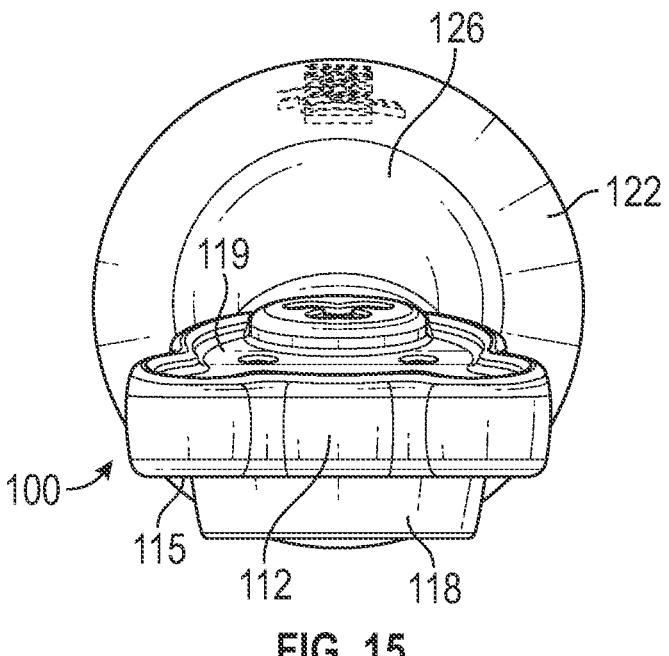
FIG. 15 is a top plan view of the oral cleaning device shown in FIG. 10.
Figure 16:
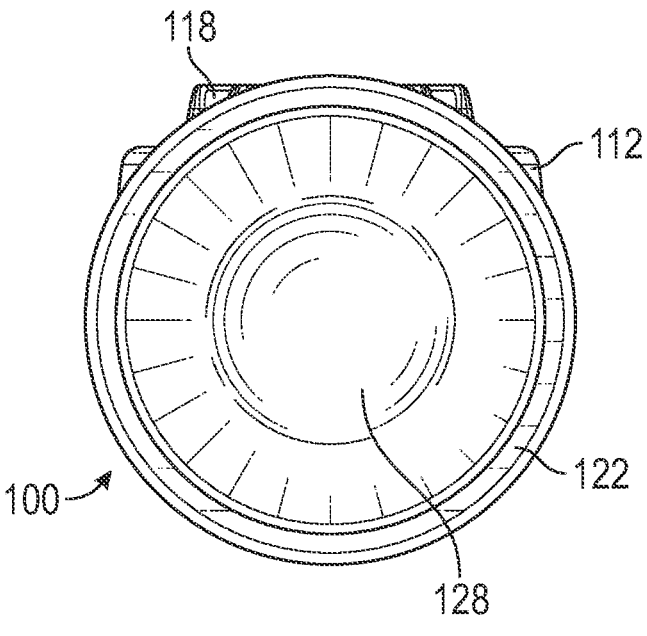
FIG. 16 is a bottom plan view of the oral cleaning device shown in FIG. 10.
Figure 17:
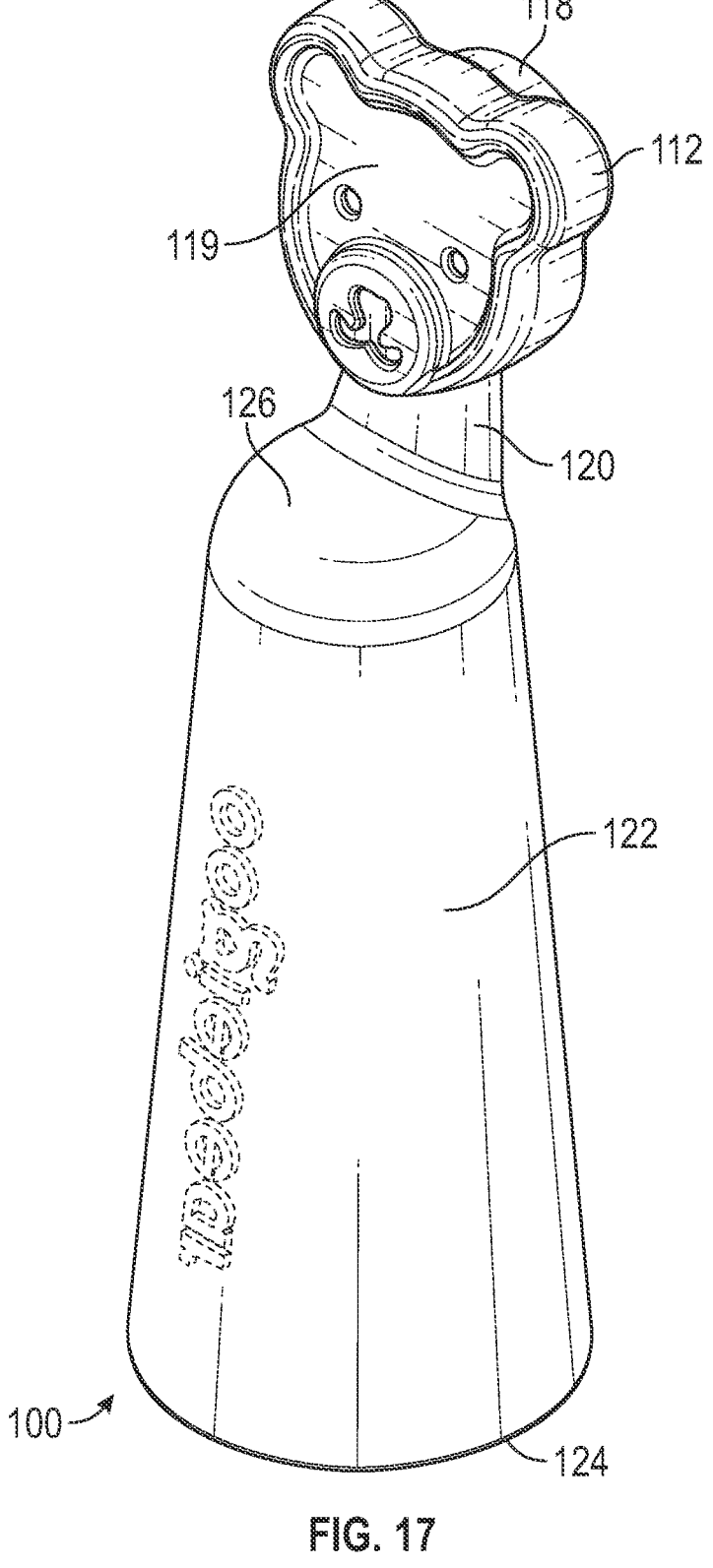
FIG. 17 is a rear perspective view of the oral cleaning device shown in FIG. 10.

With combined reference to FIGS. 13-15, it can be seen that, in the illustrative embodiment, the head portion 112 of the oral cleaning device 100 comprises a front surface 115 and a rear surface 119. The front surface 115 is oppositely disposed relative to the rear surface 119. In the illustrative embodiment, it can be seen that the head portion 112 is in a shape of an animal head (i.e., a bear head), and that the rear surface 119 of the head portion 112 comprises a face of the bear head (refer to FIGS. 12 and 17).

Figure 10:
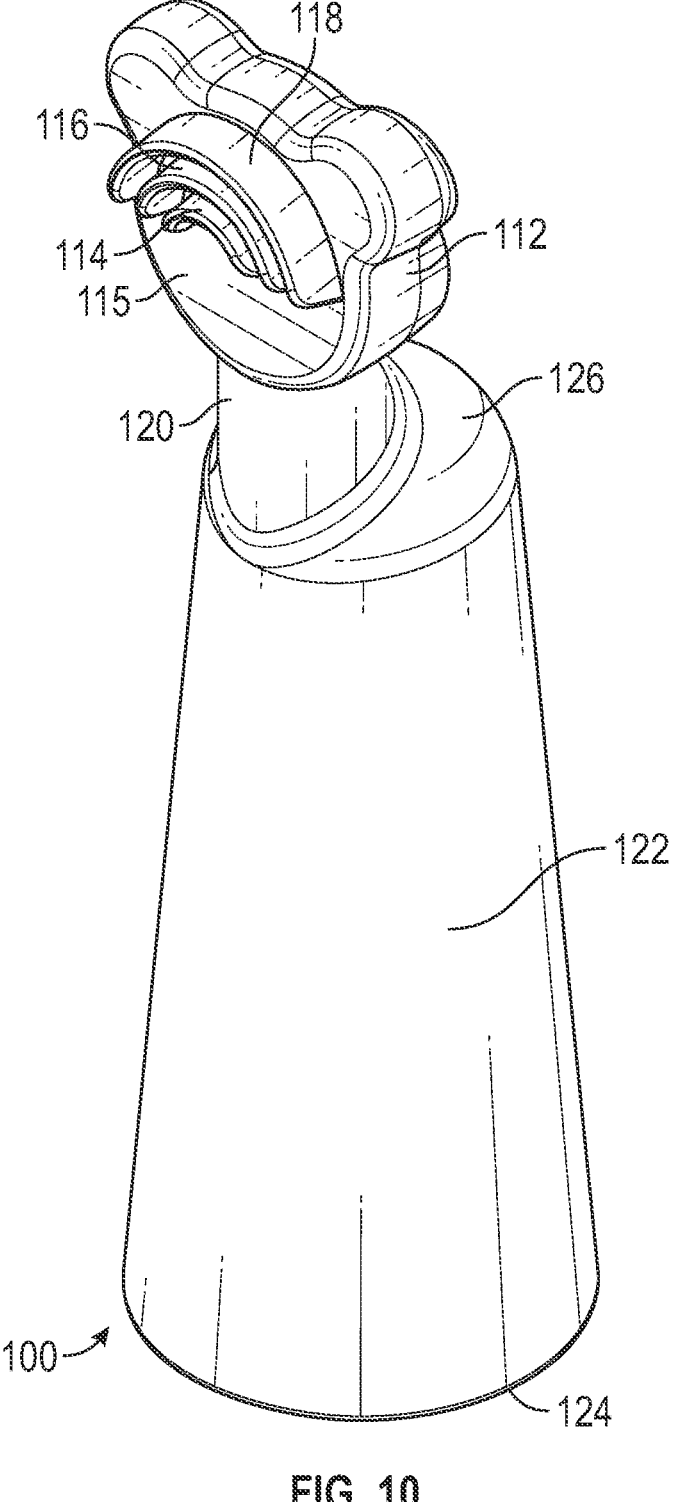
FIG. 10 is a frontal perspective view of an oral cleaning device for a baby, according to a second illustrative embodiment of the disclosure.
Figure 11:
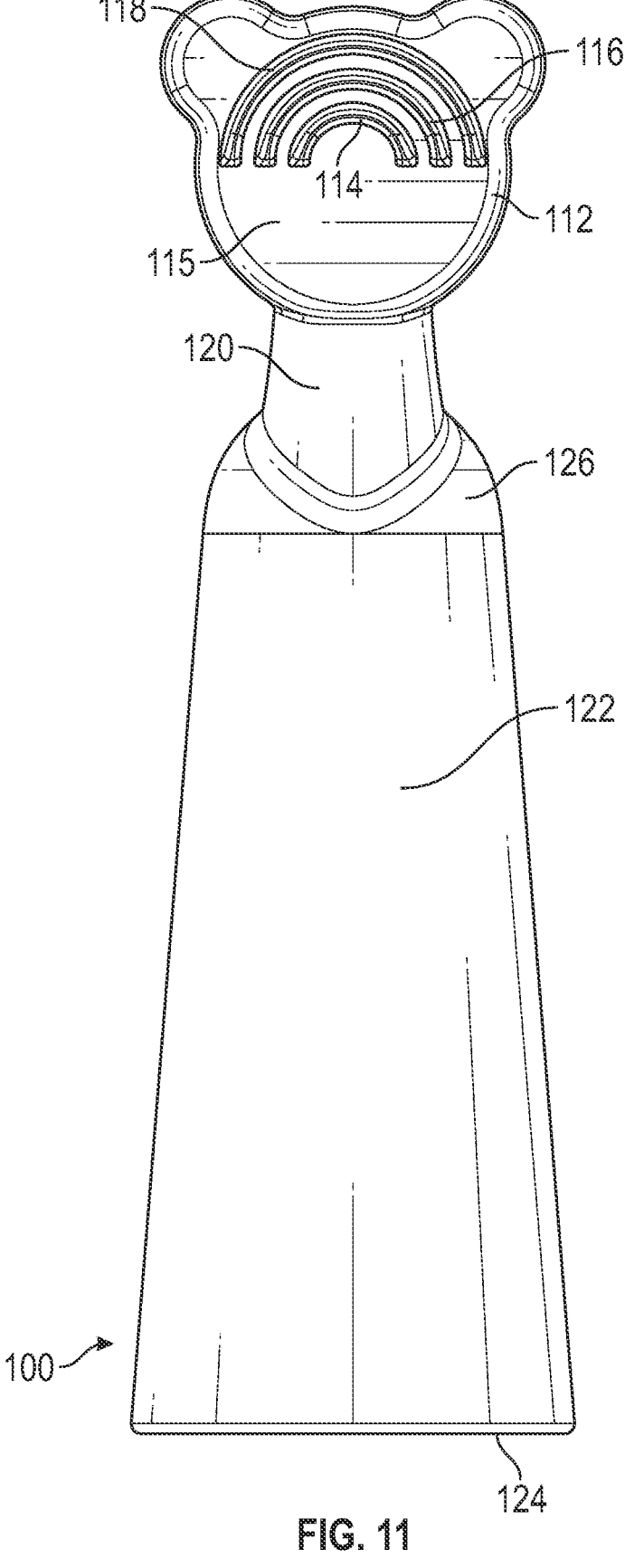
FIG. 11 is a front elevational view of the oral cleaning device shown in FIG. 10.
Figure 12:
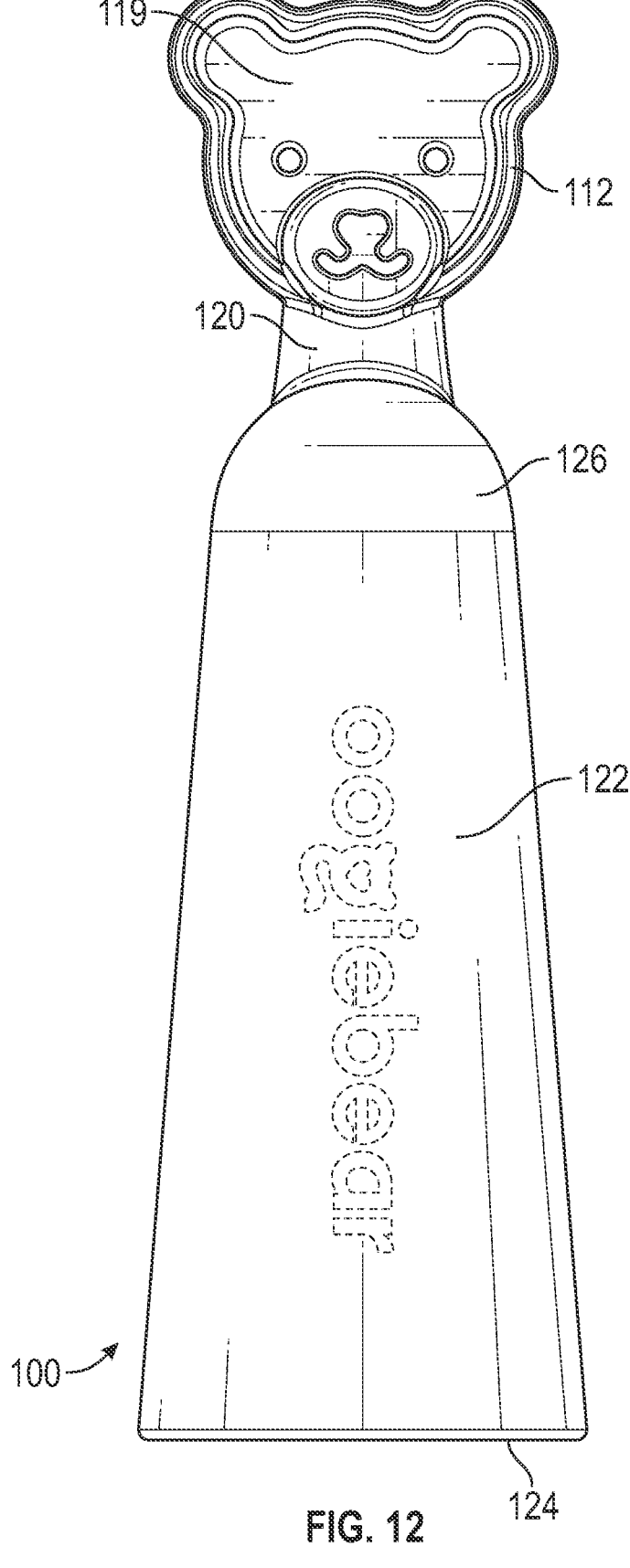
FIG. 12 is a rear elevational view of the oral cleaning device shown in FIG. 10.

In the illustrative embodiment, as shown in FIGS. 10 and 11, the at least one protrusion 114, 116, 118 is disposed on the front surface 115 of the head portion 112 of the oral cleaning device 100. Also, in the illustrative embodiment, the at least one protrusion 114, 116, 118 comprises a first protrusion 114 disposed in a central region of the front surface 115 of the head portion 112, a second protrusion 116 disposed above the first protrusion 114 on the front surface 115 of the head portion 112, and a third protrusion 118 disposed above the second protrusion 116 on the front surface 115 of the head portion 112. In the illustrative embodiment, the first protrusion 114, the second protrusion 116, and the third protrusion 118 of the head portion 112 are each semi-circular in shape (refer to FIGS. 10 and 11), and the first protrusion 114, the second protrusion 116, and the third protrusion 118 are arranged in a generally concentric arrangement (see FIG. 11). As shown in the illustrative embodiment of FIG. 11, the second protrusion 116 has a second radius that is larger than a first radius of the first protrusion 114, and the third protrusion 118 has a third radius that is larger than the second radius of the second protrusion 116.

In the illustrative embodiment, the oral cleaning device 100 is formed from a polymeric material that does not comprise latex, bisphenol A (BPA), or polyvinyl chloride (PVC) (i.e., the material is latex-free, BPA-free, and PVC-free). More specifically, in the illustrative embodiment, the polymeric material forming the oral cleaning device 100 comprises silicone that does not contain latex, BPA, or PVC.

Now, with reference to FIGS. 10, 11, and 18, the manner in which the oral cleaning device 100 of the second illustrative embodiment is used will be described. First, a user (e.g., a parent or other caregiver) inserts one of his or her fingers into the tapered finger recess 128 of the body portion 122. Advantageously, the innovative tapered design of the finger recess 128 allows varying finger sizes of different users to be snugly received within the finger recess 128 (e.g., smaller fingers are inserted further into the tapered finger recess 128, while larger fingers are not inserted as far into the tapered finger recess 128). Then, the user (e.g., a parent or other caregiver) inserts the head portion 112 of the oral cleaning device 100 into a mouth of a baby so as to clean the tongue of the baby using the protrusions 114, 116, 118 on the head portion 112. The cleaning of the baby's tongue is enhanced by the arrangement of the concentric protrusions 114, 116, 118 on the front surface 115 of the head portion 112 (i.e., because the concentric protrusions 114, 116, 118 result in better overall tongue surface coverage). The soft silicone material of the illustrative oral cleaning device 100 makes the oral cleaning device comfortable for the baby.

It is readily apparent that the aforedescribed oral cleaning device 100 offers numerous advantages. As described above, the oral cleaning device 100 is configured to accommodate varying finger sizes of different users so that the user is able to more effectively clean the tongue of a baby (i.e., the size of the finger recess 128 narrows to allow virtually any size finger to fit comfortably). Further, the oral cleaning device 100 is safe and comfortable for both the user and the baby. In the illustrative embodiment, the oral cleaning device 100 is formed from a flexible material that is gentle, safe, and firm enough to brush effectively. Also, in the illustrative embodiment, the oral cleaning device 100 is advantageously reusable, washable, and environmentally friendly.

In one or more illustrative embodiments, the aforedescribed oral cleaning device 100 helps to ensure healthy hygiene. Parents are able to begin a healthy dental hygiene regime from the beginning of their child's life so as to promote better oral health care early on. The oral cleaning device 100 is lightweight and easy to clean, which makes it handy for home or on the go. The oral cleaning device 100 is in a form of a durable, reusable tool that is made of high quality material(s) and cleans easily with soap and water. Because the head portion 112 of the oral cleaning device 100 is spaced apart from a fingertip of a user, the inadvertent biting of a user's finger is prevented by the oral cleaning device 100, thereby advantageously resulting in a pain-free cleaning experience for the user (e.g., the parent or other caregiver). Also, the head portion 112 of the oral cleaning device 100 has a size that fits easily into the baby's mouth. The tapered finger recess 128 of the body portion 122 of the oral cleaning device 100 accommodates the finger sizes of virtually all users so that the user is able to clean the tongue of the baby with great control.

Any of the features or attributes of the above described embodiments and variations can be used in combination with any of the other features and attributes of the above described embodiments and variations as desired.

Although the oral cleaning device 10, 100 has been shown and described with respect to a certain embodiment or embodiments, it is apparent that the aforedescribed oral cleaning device 10, 100 can be embodied in many different forms and that many other modifications and variations are possible without departing from the spirit and scope of the claimed invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. An oral cleaning device for a baby, comprising:
a head portion, the head portion including one of: (i) at least one plurality of bristles for brushing gums and/or teeth of a baby, or (ii) at least one protrusion for scraping food particles and other matter from a tongue of the baby;
a body portion connected to the head portion, the body portion having a first end that is distal from the head portion and a second end that is proximal to the head portion, the first end being oppositely disposed relative to the second end, the body portion including a tapered finger recess for accommodating varying finger sizes of different users, the tapered finger recess having a cross-sectional area that gradually decreases in size from the first end to the second end, the body portion further including a ledge at the second end of the body portion, wherein the body portion comprises a hemispherical end cap that defines the ledge at the second end of the body portion; and a stem portion connecting the head portion to the body portion, the stem portion extending from the second end of the body portion to the head portion so that the head portion of the oral cleaning device is spaced apart from a fingertip of a user to prevent an inadvertent biting of the fingertip of the user by the baby, the ledge of the body portion surrounding the stem portion on a plurality of sides of the stem portion, the stem portion being inwardly offset from a peripheral boundary of the ledge on the plurality of sides of the stem portion, wherein the stem portion extends asymmetrically from the second end of the body portion relative to a longitudinal centerline of the body portion, and wherein the stem portion comprises a curved base that corresponds to a curvature of the hemispherical end cap at the second end of the body portion, the curved base having a wider diameter than a remainder of the stem portion;

wherein the head portion is flared outwardly from the stem portion such that the head portion has a head width that is greater than a stem width of the stem portion.

2. The oral cleaning device according to claim 1, wherein the head portion of the oral cleaning device comprises a concave inner surface and a convex outer surface, the convex outer surface being oppositely disposed relative to the concave inner surface.

3. The oral cleaning device according to claim 2, wherein the head portion comprises the at least one plurality of bristles for brushing gums and/or teeth of the baby, and the at least one plurality of bristles are disposed on the concave inner surface of the head portion of the oral cleaning device.

4. The oral cleaning device according to claim 3, wherein the at least one plurality of bristles comprises a first plurality of bristles disposed in a central region of the concave inner surface of the head portion, a second plurality of bristles disposed in a first side region of the concave inner surface of the head portion, and a third plurality of bristles disposed in a second side region of the concave inner surface of the head portion.

5. The oral cleaning device according to claim 4, wherein the second plurality of bristles are disposed at a first acute angle relative to the first plurality of bristles, and the third plurality of bristles are disposed at a second acute angle relative to the first plurality of bristles.

6. The oral cleaning device according to claim 5, wherein the first acute angle of the second plurality of bristles is generally the same as the second acute angle of the third plurality of bristles.

7. The oral cleaning device according to claim 1, wherein the head portion of the oral cleaning device comprises a front surface and a rear surface, the front surface being oppositely disposed relative to the rear surface.

8. The oral cleaning device according to claim 7, wherein the head portion is in a shape of an animal head.

9. The oral cleaning device according to claim 8, wherein the animal head forming the head portion is a bear head.

10. The oral cleaning device according to claim 9, wherein the rear surface of the head portion comprises a face of the bear head.

11. The oral cleaning device according to claim 7, wherein the head portion comprises the at least one protrusion for scraping food particles and other matter from a tongue of the baby, and the at least one protrusion is disposed on the front surface of the head portion of the oral cleaning device.

12. The oral cleaning device according to claim 11, wherein the at least one protrusion comprises a first protrusion disposed in a central region of the front surface of the head portion, a second protrusion disposed above the first protrusion on the front surface of the head portion, and a third protrusion disposed above the second protrusion on the front surface of the head portion.

13. The oral cleaning device according to claim 12, wherein the first protrusion, the second protrusion, and the third protrusion of the head portion are each semi-circular in shape, and the first protrusion, the second protrusion, and the third protrusion are arranged in a generally concentric arrangement.

14. The oral cleaning device according to claim 13, wherein the second protrusion has a second radius that is larger than a first radius of the first protrusion, and the third protrusion has a third radius that is larger than the second radius of the second protrusion.

15. The oral cleaning device according to claim 1, wherein the tapered finger recess comprises a hemispherical end portion proximate to the second end of the body portion of the oral cleaning device.

16. The oral cleaning device according to claim 1, wherein the oral cleaning device is formed from a polymeric material.

17. The oral cleaning device according to claim 16, wherein the polymeric material forming the oral cleaning device comprises silicone.

18. The oral cleaning device according to claim 16, wherein the polymeric material forming the oral cleaning device does not comprise latex, bisphenol A, or polyvinyl chloride.

* * * * *